(12) United States Patent
Lee et al.

(10) Patent No.: US 10,448,847 B2
(45) Date of Patent: *Oct. 22, 2019

(54) SYSTEM AND METHOD FOR CAMERA-BASED HEART RATE TRACKING

(71) Applicant: NURALOGIX CORPORATION, Toronto (CA)

(72) Inventors: Kang Lee, Toronto (CA); Evgueni Kabakov, North York (CA); Phil Levy, Brampton (CA)

(73) Assignee: NURALOGIX CORPORATION, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/153,214

(22) Filed: Oct. 5, 2018

(65) Prior Publication Data

US 2019/0038159 A1 Feb. 7, 2019

Related U.S. Application Data

(63) Continuation of application No. 15/923,242, filed on Mar. 16, 2018, now Pat. No. 10,117,588, which is a
(Continued)

(51) Int. Cl.
*G06K 9/00* (2006.01)
*A61B 5/024* (2006.01)
(Continued)

(52) U.S. Cl.
CPC .......... *A61B 5/02427* (2013.01); *A61B 5/024* (2013.01); *A61B 5/026* (2013.01);
(Continued)

(58) Field of Classification Search
None
See application file for complete search history.

(56) References Cited

U.S. PATENT DOCUMENTS

2011/0251493 A1 10/2011 Poh et al.
2015/0190061 A1 7/2015 Godavarty et al.
(Continued)

OTHER PUBLICATIONS

International Search Report corresponding to PCT/CA2017/051354 dated Jan. 31, 2018.
(Continued)

*Primary Examiner* — Atiba O Fitzpatrick
(74) *Attorney, Agent, or Firm* — Anil Bhole; Marc Lampert; Bhole IP Law

(57) ABSTRACT

A system and method for camera-based heart rate tracking. The method includes: determining bit values from a set of bitplanes in a captured image sequence that represent the HC changes; determining a facial blood flow data signal for each of a plurality of predetermined regions of interest (ROIs) of the subject captured by the images based on the HC changes; applying a band-pass filter of a passband approximating the heart rate to each of the blood flow data signals; applying a Hilbert transform to each of the blood flow data signals; adjusting the blood flow data signals from revolving phase-angles into linear phase segments; determining an instantaneous heart rate for each the blood flow data signals; applying a weighting to each of the instantaneous heart rates; and averaging the weighted instantaneous heart rates.

20 Claims, 5 Drawing Sheets

Related U.S. Application Data continuation of application No. PCT/CA2017/051354, filed on Nov. 14, 2017.

(60) Provisional application No. 62/421,517, filed on Nov. 14, 2016.

(51) Int. Cl.
| | | |
|---|---|---|
| *G06N 20/00* | (2019.01) | |
| *A61B 5/026* | (2006.01) | |
| *A61B 5/1455* | (2006.01) | |
| *G16H 30/40* | (2018.01) | |
| *G16H 50/20* | (2018.01) | |
| *A61B 5/0255* | (2006.01) | |
| *A61B 5/00* | (2006.01) | |
| *G06T 7/00* | (2017.01) | |
| *A61B 5/145* | (2006.01) | |

(52) U.S. Cl.
CPC .......... *A61B 5/0255* (2013.01); *A61B 5/0261* (2013.01); *A61B 5/02416* (2013.01); *A61B 5/1455* (2013.01); *A61B 5/725* (2013.01); *A61B 5/7253* (2013.01); *A61B 5/7267* (2013.01); *A61B 5/7278* (2013.01); *A61B 5/7485* (2013.01); *G06N 20/00* (2019.01); *G06T 7/0016* (2013.01); *G16H 30/40* (2018.01); *G16H 50/20* (2018.01); *A61B 5/0077* (2013.01); *A61B 5/14546* (2013.01); *A61B 2576/00* (2013.01); *G06T 2207/20081* (2013.01); *G06T 2207/30104* (2013.01)

(56) References Cited

U.S. PATENT DOCUMENTS

| | | |
|---|---|---|
| 2016/0098592 A1 | 4/2016 | Lee et al. |
| 2016/0220192 A1 | 8/2016 | Wiggins et al. |
| 2017/0156673 A1* | 6/2017 | Uchida ............... A61B 5/6893 |
| 2019/0008392 A1* | 1/2019 | Wang ..................... A61B 5/00 |

OTHER PUBLICATIONS

Written Opinion of the International Searching Authority corresponding to PCT/CA2017/051354 dated Jan. 31, 2018.

Lee at al, "Face and palmprint multimodal biometric system based on bit-plane decomposition approach" IEEE 2016 International Conference on Consumer Electronics—Taiwan (ICCE-TW), May 27, 2016.

Bogdan, Gavriloaia, et al. "Remote assessment of heart rate by skin color processing." 2015 IEEE Black Sea Conference on Communications and Networking (BlackSeaCom), May 18, 2015.

Iozzia, L et al., "Assessment of beat-to-beat heart rate detection method using a camera as contactless sensor." 2016IEEE 38th Annual International Conference of the Engineering in Medicine and Biology Society (EMBC), Aug. 16, 2016.

Osman, A. et al., "Supervised learning approach to remote heart rate estimation from facial videos." 11th IEEE International Conference and Workshops on Automatic Face and Gesture Recognition (FG), vol. 1, May 4, 2015.

Seal, Ayan, et al. "Automated thermal face recognition based on minutiae extraction." International Journal of Computational Intelligence Studies 2.2., Jan. 31, 2013.

* cited by examiner

SYSTEM AND METHOD FOR CAMERA-BASED HEART RATE TRACKING

TECHNICAL FIELD

The following relates generally to detection of a human heartbeat and more specifically to a system and method for camera-based heart rate tracking.

BACKGROUND

The human heartbeat, or cardiac cycle, represents one of the primary vital signs monitored by health care providers and members of the general public alike. Heartbeat, as used herein, refers to a complete heartbeat, or a set of heartbeats, from its generation to the beginning of the next beat; thus, it includes the diastole, the systole, and the intervening pause. The pace of the heartbeats, referred to herein as the heart rate, is a measure of cardiac cycles per time period. Heart rate is typically measured in beats-per-minute (BPM) as a measure of, on average, how many cardiac cycles occur per minute. The BPM measurement can be an average heart rate, measuring the average BPM over a sizeable period of cardiac cycles, or an instantaneous heart rate, measuring the BPM over a short period of cardiac cycles and extrapolating out the BPM.

Conventionally, the heart rate is measured using equipment such as an electrocardiogram by recording the electrical activity of the heart over a period of time using electrodes placed on the skin. This approach is a significant expense and requires invasive electrodes to be placed on a subject. Other conventional approaches include attaching a heart rate monitor to a subject, which typically includes a chest strap transmitter and a receiver. This approach is not particularly accurate and susceptible to noise, and in addition, requires the subject to place the transmitter under his/her clothes. Further types of strapless heart rate monitors allow the measurement of the heart rate with a wearable device, such as a wristwatch or finger clasp, by utilising an infrared sensor to measure the heart rate. However, such devices do not provide much detail and are not particularly accurate.

SUMMARY

In an aspect, there is provided a method for camera-based heart rate tracking of a human subject, the method comprising: receiving a captured image sequence of light re-emitted from the skin of the human subject; determining, using a machine learning model trained with a hemoglobin concentration (HC) changes training set, bit values from a set of bitplanes in the captured image sequence that represent the HC changes of the subject, the set of bitplanes being those that are determined to approximately maximize a signal-to-noise ratio (SNR), the HC changes training set comprising bit values from each bitplane of images captured from a set of subjects for which heart rate is known; determining a facial blood flow data signal for each of a plurality of predetermined regions of interest (ROIs) of the subject captured by the images based on the HC changes; applying a band-pass filter of a passband approximating the heart rate to each of the blood flow data signals; applying a Hilbert transform to each of the blood flow data signals; adjusting the blood flow data signals from revolving phase-angles into linear phase segments; determining an instantaneous heart rate for each the blood flow data signals; applying a weighting to each of the instantaneous heart rates; averaging the weighted instantaneous heart rates; and outputting the average heart rate.

In a particular case, the ROIs are captured from the face of the subject.

In another case, the ROIs are captured from the wrist or the neck of the subject.

In yet another case, the ROIs are non-overlapping.

In yet another case, determining a set of bitplanes that maximize SNR comprises: performing pixelwise image subtraction and addition of bitplane vectors to maximize signal differences in all ROIs over a predetermined time period, and identifying bit values from bitplanes that increase the signal differentiation and bit values from bitplanes that decrease the signal differentiation or do not contribute to signal differentiation; and discarding the bit values from the bitplanes that decrease the signal differentiation or do not contribute to signal differentiation.

In yet another case, the machine learning model comprises a Long Short Term Memory (LSTM) neural network or a non-linear Support Vector Machine.

In yet another case, the passband is in a range of approximately 0.6 hertz to 1.2 hertz, where 60 heartbeats-per-minute is equivalent to 1 hertz.

In yet another case, determining the instantaneous heart rate for each the blood flow data signals comprises applying a differential filter to the linear phase segments to convert the phase-angle data into frequency units representing a count value, the count value for each of the ROIs represents the instantaneous heart rate.

In yet another case, the method further comprising linearizing and differentiating the revolving phase-angles on a phase continuum scale to determine the instantaneous heart rate.

In yet another case, the weighting is integrated over an interval in the range of approximately one second to ten seconds.

In yet another case, the weighting is integrated over an interval of approximately five seconds.

In another aspect, there is provided a system for camera-based heart rate tracking of a human subject, the system comprising one or more processors and a data storage device, the one or more processors configured to execute: a TOI module to receive a captured image sequence of light re-emitted from the skin of a human subject, the TOI module determines, using a machine learning model trained with a hemoglobin concentration (HC) changes training set, bit values from a set of bitplanes in the captured image sequence that represent the HC changes of the subject, the set of bitplanes being those that are determined to approximately maximize a signal-to-noise ratio (SNR), the HC changes training set comprising bit values from each bitplane of images captured from a set of subjects for which heart rate is known, the TOI module determines a facial blood flow data signal for each of a plurality of predetermined regions of interest (ROIs) of the subject captured by the images based on the HC changes; a filtering module to apply a band-pass filter of a passband approximating the heart rate to each of the blood flow data signals; a Hilbert transform module to apply a Hilbert transform to each of the blood flow data signals; an adjustment module to adjust the blood flow data signals from revolving phase-angles into linear phase segments; a derivative module to determine an instantaneous heart rate for each the blood flow data signals; a weighting module to apply a weighting to each of the instantaneous heart rates; a summation module to average the weighted instantaneous heart rates; and an output module to output the average heart rate.

In a particular case, the ROIs are captured from the face of the subject.

In another case, the ROIs are non-overlapping.

In yet another case, the TOI module determines a set of bitplanes that maximize SNR by: performing pixelwise image subtraction and addition of bitplane vectors to maximize signal differences in all ROIs over a predetermined time period, and identifying bit values from bitplanes that increase the signal differentiation and bit values from bitplanes that decrease the signal differentiation or do not contribute to signal differentiation; and discarding the bit values from the bitplanes that decrease the signal differentiation or do not contribute to signal differentiation.

In yet another case, the passband is in a range of approximately 0.6 hertz to 1.2 hertz, where 60 heartbeats-per-minute is equivalent to 1 hertz.

In yet another case, the derivative module determines the instantaneous heart rate for each the blood flow data signals by applying a differential filter to the linear phase segments to convert the phase-angle data into frequency units representing a count value, the count value for each of the ROIs represents the instantaneous heart rate.

In yet another case, the derivative module linearizes and differentiates the revolving phase-angles on a phase continuum scale to determine the instantaneous heart rate.

In yet another case, the weighting applied by the weighting module is integrated over an interval in the range of approximately one second to ten seconds.

In yet another case, the weighting applied by the weighting module is integrated over an interval of approximately five seconds.

These and other aspects are contemplated and described herein. It will be appreciated that the foregoing summary sets out representative aspects of camera-based heart rate tracking systems and methods for the determination of heart rate to assist skilled readers in understanding the following detailed description.

BRIEF DESCRIPTION OF THE DRAWINGS

The features of the invention will become more apparent in the following detailed description in which reference is made to the appended drawings wherein.

DETAILED DESCRIPTION

Figure 1:
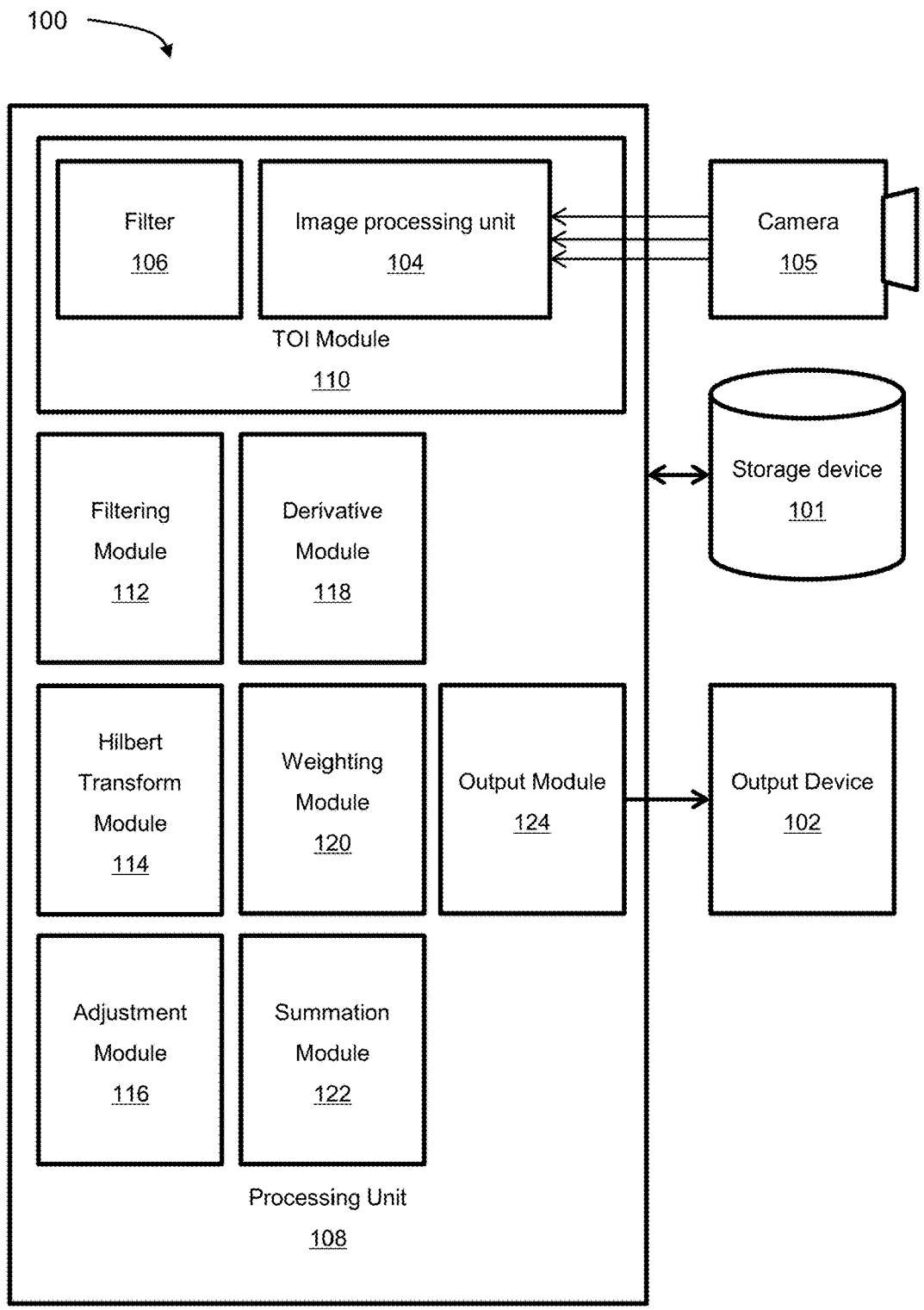
FIG. 1 is an block diagram of a system for camera-based heart rate tracking, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to detection of a human heartbeat and more specifically to a system and method for camera-based heart rate tracking. Heart rate is determined using image processing techniques performed over a plurality of images captured by one or more digital imaging cameras.

In embodiments of the system and method described herein, technical approaches are provided to solve the technological problem of detecting and tracking a human's heartbeat. The technical approaches described herein offer the substantial advantages of both 'spatial' diversity, where region of interest (ROI) signals are acquired from non-overlapping differentially located regions on a human's face, and 'time' diversity, where accumulation of time-series data is simultaneously sampled with synchronous or fixed timing. Applicant recognized the significant advantages of this approach, for example, being that the quality of the beatsper-minute (BPM) estimate is more robust to noise interference (for example due to outlier data) while retaining the ability to update the output BPM value at every sample interval (for example at the video frame rate).

Applicant further recognized the significant advantages of the technical approaches described herein, for example, by utilizing machine learning techniques, the composition of bitplanes of video images can be optimized to maximize the signal to noise ratio of the heart rate band, especially as compared to conventional approaches.

Referring now to FIG. 1, a system for camera-based heart rate tracking 100 is shown. The system 100 includes a processing unit 108, one or more video-cameras 105, a storage device 101, and an output device 102. The processing unit 108 may be communicatively linked to the storage device 101 which may be preloaded and/or periodically loaded with video imaging data obtained from one or more video-cameras 105. The processing unit 108 includes various interconnected elements and modules, including a TOI module 110, a filtering module 112, a Hilbert transform module 114, an adjustment module 116, a derivative module 118, a weighting module 120, a summation module 122, and an output module 124. The TOI module includes an image processing unit 104 and a filter 106. The video images captured by the video-camera 105 can be processed by the filter 106 and stored on the storage device 101. In further embodiments, one or more of the modules can be executed on separate processing units or devices, including the video-camera 105 or output device 102. In further embodiments, some of the features of the modules may be combined or run on other modules as required.

The term "video", as used herein, can include sets of still images. Thus, "video camera" can include a camera that captures a sequence of still images.

Figure 3:
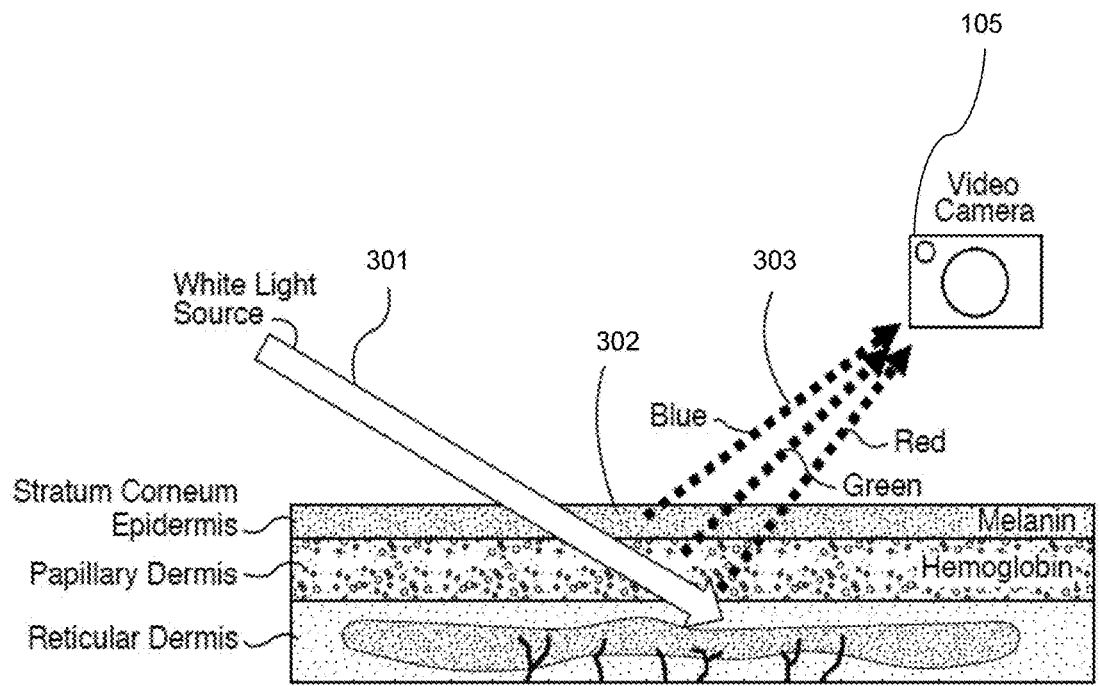
FIG. 3 illustrates re-emission of light from skin epidermal and subdermal layers.
Figure 4:
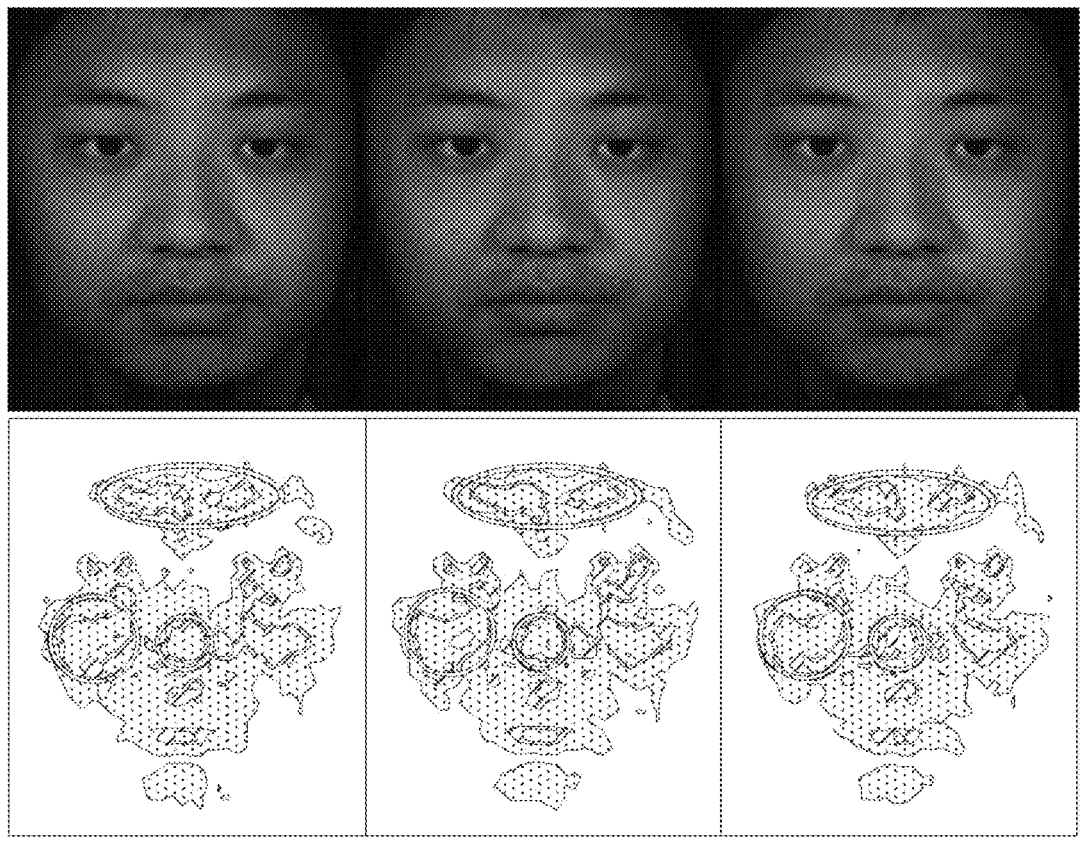
FIG. 4 is a set of surface and corresponding transdermal images illustrating change in hemoglobin concentration for a particular human subject at a particular point in time.

Using transdermal optical imaging (TOI), the TOI module 110 can isolate hemoglobin concentration (HC) from raw images taken from a traditional digital camera. Referring now to FIG. 3, a diagram illustrating the re-emission of light from skin is shown. Light 301 travels beneath the skin 302, and re-emits 303 after travelling through different skin tissues. The re-emitted light 303 may then be captured by optical cameras 105. The dominant chromophores affecting the re-emitted light are melanin and hemoglobin. Since melanin and hemoglobin have different color signatures, it has been found that it is possible to obtain images mainly reflecting HC under the epidermis as shown in FIG. 4.

Using transdermal optical imaging (TOI), the TOI module 110, via the image processing unit 104, obtains each captured image or video stream, from the camera 105, and performs operations upon the image to generate a corresponding optimized hemoglobin concentration (HC) image of the subject. From the HC data, the facial blood flow localized volume concentrations can be determined; whereby localized volume concentrations refer to measured HC intensity values within a region of interest. As described, regions of interest are used to define a localized bounded area, or areas, for which HC is to be measured The image processing unit 104 isolates HC in the captured video sequence. In an exemplary embodiment, the images of the subject's faces are taken at 30 frames per second using a digital camera 105. It will be appreciated that this process may be performed with alternative digital cameras, lighting conditions, and frame rates.

Isolating HC is accomplished by analyzing bitplanes in the video sequence to determine and isolate a set of the bitplanes that approximately maximize the signal to noise ratio (SNR). The determination of high SNR bitplanes is made with reference to an HC training set of images constituting the captured video sequence, in some cases, supplied along with EKG, pneumatic respiration, blood pressure, laser Doppler data collected from the human subjects from which the training set is obtained.

The regions of interest (ROIs) of the human subject's face, for example forehead, nose, and cheeks, may be defined as stationary or dynamically updated using the video images. The ROIs are preferably non-overlapping. These ROIs are preferably selected on the basis of knowledge in the art in respect of ROIs for which HC is particularly indicative of heart rate tracking (for example, forehead, cheek, or the like). Using native images that consist of all bitplanes (typically 24 bitplanes for each color image), signals that change over a particular time period (for example, 10 seconds) on each of the ROIs are extracted. In some cases, the dynamically updated ROIs can be chosen and/or maintained by using face-tracking software.

Bitplanes are a fundamental aspect of digital images. Typically, a digital image consists of certain number of pixels (for example, a width×height of 1920×1080 pixels). Each pixel of the digital image having one or more channels (for example, color channels red, green, and blue (RGB)). Each channel having a dynamic range, typically 8 bits per pixel per channel, but occasionally 10 bits per pixel per channel for high dynamic range images. Whereby, an array of such bits makes up what is known as the bitplane. In an example, for each image of color videos, there can be three channels (for example, red, green, and blue (RGB)) with 8 bits per channel. Thus, for each pixel of a color image, there are typically 24 layers with 1 bit per layer. A bitplane in such a case is a view of a single 1-bit map of a particular layer of the image across all pixels. For this type of color image, there are therefore typically 24 bitplanes (i.e., a 1-bit image per plane). Hence, for a 1-second color video with 30 frames per second, there are at least 720 (30×24) bitplanes. In the embodiments described herein, Applicant recognized the advantages of using bit values for the bitplanes rather than using, for example, merely the averaged values for each channel. Thus, a greater level of accuracy can be achieved for making predictions of HC changes, and as described making predictions of heart rate, because employing bitplanes provides a greater data basis for training the machine learning model.

The raw signals can be pre-processed using one or more filters, depending on the signal characteristics. Such filters may include, for example, a Butterworth filter, a Chebycheff filter, or the like. Using the filtered signals from two or more ROIs, machine learning is employed to systematically identify bitplanes that will significantly increase the signal differentiation (for example, where the SNR improvement is greater than 0.1 db) and bitplanes that will contribute nothing or decrease the signal differentiation. After discarding the latter, the remaining bitplane images can optimally determine the bold flow.

The machine learning process involves manipulating the bitplane vectors (for example, 24 bitplanes×60 hz) using the bit value in each pixel of each bitplane along the temporal dimension. In one embodiment, this process requires subtraction and addition of each bitplane to maximize the signal differences in all ROIs over the time period. In some cases, to obtain reliable and robust computational models, the entire dataset can be divided into three sets: the training set (for example, 80% of the whole subject data), the test set (for example, 10% of the whole subject data), and the external validation set (for example, 10% of the whole subject data). The time period can vary depending on the length of the raw data (for example, 15 seconds, 60 seconds, or 120 seconds). The addition or subtraction is performed in a pixel-wise manner. An existing machine learning algorithm, the Long Short Term Memory (LSTM) neural network, or a suitable alternative thereto is used to efficiently and obtain information about the improvement of differentiation in terms of accuracy, which bitplane(s) contributes the best information, and which does not in terms of feature selection. The Long Short Term Memory (LSTM) neural network allow us to perform group feature selections and classifications. The LSTM machine learning algorithm are discussed in more detail below. From this process, the set of bitplanes to be isolated from image sequences to reflect temporal changes in HC is obtained. An image filter is configured to isolate the identified bitplanes as described below.

To extract facial blood flow data, facial HC change data on each pixel of each subject's face image is extracted as a function of time when the subject is being viewed by the camera 105. To increase signal-to-noise ratio (SNR), the subject's face is divided into a plurality of regions of interest (ROIs) according to, for example, their differential underlying physiology, and the data in each ROI is averaged.

Machine learning approaches (such as a Long Short Term Memory (LSTM) neural network, or a suitable alternative such as non-linear Support Vector Machine) and deep learning may be used to assess the existence of common spatial-temporal patterns of hemoglobin changes across subjects (for example, differences in amplitude in blood flow changes in the forehead and the cheek over time). In some cases, the Long Short Term Memory (LSTM) neural network, or an alternative, can be trained on the transdermal data from a portion of the subjects (for example, 80%, or 90% of the subjects) to obtain a computational model for the facial blood flow, which can be tested using the test data set and externally validated using the external validation data set.

Once the model is trained as described, it becomes possible to obtain a video sequence of any subject and apply the HC extracted from selected bitplanes to the computational models to determine blood flow. For long running video streams with changes in blood flow and intensity fluctuations, changes of the estimation and intensity scores over time relying on HC data based on a moving time window (e.g., 10 seconds) may be reported.

Figure 5:
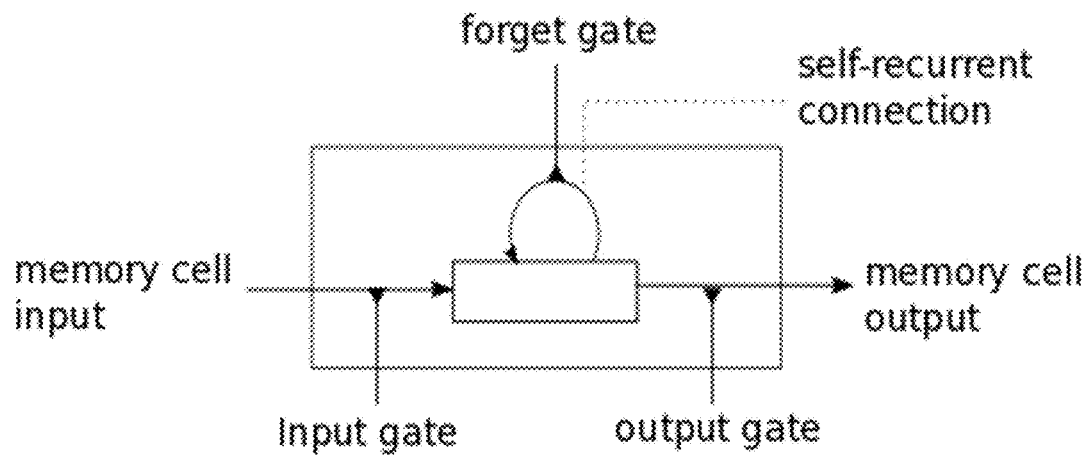
FIG. 5 is a diagrammatic representation of a memory cell.

In an example using the Long Short Term Memory (LSTM) neural network, the LSTM neural network comprises at least three layers of cells. The first layer is an input layer, which accepts the input data. The second (and perhaps additional) layer is a hidden layer, which is composed of memory cells (see FIG. 5). The final layer is output layer, which generates the output value based on the hidden layer using Logistic Regression.

Each memory cell, as illustrated, comprises four main elements: an input gate, a neuron with a self-recurrent connection (a connection to itself), a forget gate and an output gate. The self-recurrent connection has a weight of 1.0 and ensures that, barring any outside interference, the state of a memory cell can remain constant from one time step to another. The gates serve to modulate the interactions between the memory cell itself and its environment. The input gate permits or prevents an incoming signal to alter the state of the memory cell. On the other hand, the output gate can permit or prevent the state of the memory cell to have an effect on other neurons. Finally, the forget gate can modulate the memory cell's self-recurrent connection, permitting the cell to remember or forget its previous state, as needed.

The equations below describe how a layer of memory cells is updated at every time step t. In these equations: $x_t$ is the input array to the memory cell layer at time t. In our application, this is the blood flow signal at all ROIs $$\vec{x}_t = [x_{1t}, x_{2t} \ldots x_{nt}]$$

$W_i$, $W_f$, $W_c$, $W_o$, $U_i$, $U_f$, $U_c$, $U_o$ and $V_o$ are weight matrices; and
$b_i$, $b_f$, $b_c$ and $b_o$ are bias vectors First, we compute the values for $i_t$, the input gate, and $\tilde{C}_t$ the candidate value
for the states of the memory cells at time t:

$$i_t = \sigma(W_i x_t + U_i h_{t-1} + b_i)$$

$$\tilde{C}_t = \tan h(W_c x_t + U_c h_{t-1} + b_c)$$

Second, we compute the value for $f_t$, the activation of the memory cells' forget gates at time t:

$$f_t = \sigma(W_f x_t + U_f h_{t-1} + b_f)$$

Given the value of the input gate activation $i_t$, the forget gate activation $f_t$ and the candidate state value $\tilde{C}_t$, we can compute $C_t$ the memory cells' new state at time t:

$$C_t = i_t * \tilde{C}_t + f_t * C_{t-1}$$

With the new state of the memory cells, we can compute the value of their output gates and, subsequently, their outputs:

$$o_t = \sigma(W_o x_t + U_o h_{t-1} + V_o C_t + b_o)$$

$$h_t = o_t * \tan h(C_t)$$

Based on the model of memory cells, for the blood flow distribution at each time step, we can calculate the output from memory cells. Thus, from an input sequence $x_0, x_1, x_2, \ldots, x_n$, the memory cells in the LSTM layer will produce a representation sequence $h_0, h_1, h_2, \ldots, h_n$.

The goal is to classify the sequence into different conditions. The Logistic Regression output layer generates the probability of each condition based on the representation sequence from the LSTM hidden layer. The vector of the probabilities at time step t can be calculated by:

$$p_t = \mathrm{softmax}(W_{output} h_t + b_{output})$$

where $W_{output}$ is the weight matrix from the hidden layer to the output layer, and $b_{output}$ is the bias vector of the output layer. The condition with the maximum accumulated probability will be the predicted condition of this sequence.

The heart rate tracking approach, used by the system 100 on the HC change data from the TOI module 110, utilizes adaptive weighting of multiple regions-of-interest (ROIs), and uses minimizing 'noise' criteria to control the weights. The heart rate tracking approach also utilizes a Hilbert transform to extract a coherent signal for the heartbeat. Advantageously, the accuracy when measured against 'ground truth' electrocardiogram (ECG) data indicates that the estimated "beats-per-minute" (BPM) of the heartbeat recovery approach to be typically consistent within +/−2 BPM of the ECG data.

The blood flow localized volume concentrations data captured by the TOI module 110, as described herein, of a human subject's face, as either 'live' or previously recorded, is used as the source data for determining the subject's heart rate. The facial blood flow data can then be used for estimation of related parameters such as the average heart rate in BPM.

The blood flow data signal is specified by the interpretation of the HC changes. As an example, the system 100 can monitor stationary HC changes contained by a selected ROI over time, by observing (or graphing) the resulting temporal profile (for example, shape) of the selected ROI HC intensity values over time. In some cases, the system 100 can monitor more complex migrating HC changes across multiple ROIs by observing (or graphing) the spatial dispersion (HC distribution between ROIs) as it evolves over time.

In order to estimate the BPM of the human subject, the TOI module 110 detects, recovers and tracks the valid occurrences of the subject's heartbeat. The system 100 through its various modules, as described herein, then converts these periodic occurrences into an instantaneous statistic representing the average count as BPM. This instantaneous statistic is then continuously updated. Advantageously, this approach has data-sampling that is equal to the video acquisition frame-rate specified as "frames-per-second" (FPS). This provides a continuous per-frame estimation of the instantaneous heart rate.

Figure 2:
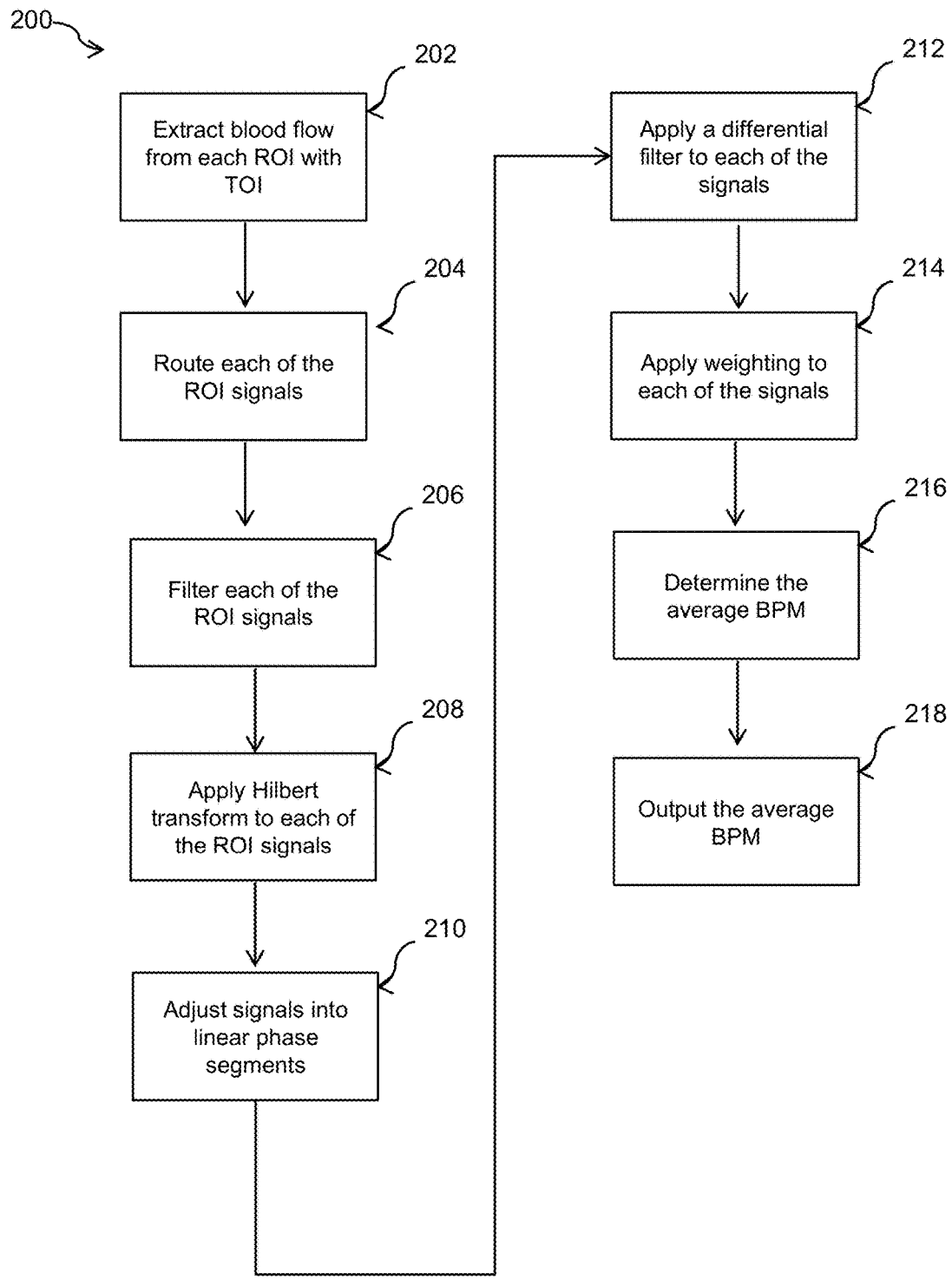
FIG. 2 is a flowchart for a method for camera-based heart rate tracking, according to an embodiment.

Turning to FIG. 2, a flowchart for a method for camera-based heart rate tracking 200 is shown.

At block 202, facial blood flow is extracted from the video using transdermal optical imaging by the TOI module 110, as described herein, for localized volume concentrations at defined regions-of-interest (ROI) on the face. In addition, the TOI module 110 records dynamic changes of such localized volume concentrations over time.

At block 204, the blood flow volume concentrations data from each ROI are treated by the filtering module 112 as an independent signal. Thus, the blood flow data for each ROI is routed through a separate, individual corresponding signal processing path (also known as chain) which handles the specific TOI signal originating from a unique location on the facial image. In this way, multiple ROIs are generating multiple signals which are independently yet concurrently processed, as a bank of ROI signal chains, using the digital signal processing (DSP) techniques described herein.

In an example, the face can be divided into 17 different regions of interest according to facial anatomy or the underlying distributions of facial vasculature (for example, the nose, the forehead, and the like). In this case, there will be 17 separate ROI signal chains, each processing a unique signal extracted from the facial image. The grouping of these 17 ROI signal chains is collectively referred to as a bank of ROI chains. As will be described, the signal processing of each ROI signal chain can be identical across all the ROIs, such that the same operations are concurrently being applied to each separate ROI signal path.

The dimension spanning across multiple ROIs will be referred to herein as a spatial diversity axis of the ROI signal banks. Each ROI signal chain includes an incoming stream of images, such as from a video camera, separated by an interval period (as described herein). The dimension spanning across images for each of the ROI signal chains, along the time dimension, will be referred to herein as the time diversity axis.

At block 206, the filtering module 112 routes each of the ROI blood flow signals to its corresponding position in a bank of digital band-pass-filters (BPF) for processing. The passband for these filters is chosen to cover the extended frequency range representing the heart-rate (where 60 bpm=1 bps=1 hz). This filtering of the signal is required to reduce energy content outside of a period of the heart-rate and thereby improving the signal-to-noise ratio (SNR). In an example, an initial heart-band passband range can extend between 0.6 hertz to 1.2 hertz. Although each individual ROI signal is filtering the heart beat from a spatially unique location on the face, the subject heart beat can be a global signal. Therefore, in some cases, a common subject-specific period can be observed across all ROIs of the subject. Thus, in some cases, the active passband for all ROIs can also be dynamically and adaptively adjusted to a common range.

Each of the filtered ROI signals, represented as a time-series, are then received, at block 208, by the Hilbert transform module 114. The Hilbert transform module 114 applies a Hilbert transform (HT) to the filtered signal. Each ROI signal is thus converted to its analytic (complex) equivalent signal attributes and decomposed as both instantaneous amplitude and instantaneous phase.

At block 210, the instantaneous phase components for each ROI signal in the signal bank are adjusted, by the adjustment module 116, from revolving phase-angles into linear phase segments in order to resolve absolute timing differences. Since the sampling steps are constant intervals, for example at the video frame rate, the rate of change between discrete instantaneous phase steps can represent a frequency. In this case, the frequency is equivalent to an integer count of the heartbeat events (occurrences) over the specified interval. To determine the rate of change between discrete instantaneous phase steps, at block 212, the instantaneous phase profile for each ROI signal is routed to the derivative module 118, which applies a differential filter, to convert the phase-angle information into frequency units (also called event units), which represent a statistic count value. This count value per ROI reflects the instantaneous BPM estimate as a continuous signal.

In this case, due to the captured sampling data coming from a stream of video images with a consistent frame-rate, accurate phase-angles can be determined based on a known timing reference, which in this case is the frames-per-second. The phase angles can then be linearized on a phase continuum scale, and the phase steps can be differentiated on the phase continuum scale to determine the frequency. This frequency is effectively the rate of heartbeat occurrences, also known as the heart rate. For proper determination of the heart rate, the sampling rate needs to have finer granularity than the measured quantity, the heart rate. In this case, processing at the video frame-rate (fps) satisfies this condition.

Phase angles can be linearized (or compensated) through a process known as "unwrapping" or "unfolding" the continuously overlapping range of phase angle response (0 to 2*pi radians). This linearization process ensures the correct accumulation of the "rotating" phase angles whenever normalizing the total phase delay which may exceed one period (2*pi) of the signal frequency. After this normalization all phase delays from various ROIs may be directly compared against each other At block 214, the weighting module 120 then applies a weighting to each of the differentially filtered signals. In a particular case, the weighting module 120 applies the following weighting to each of the differentially filtered ROI signals: $W(i)=1/(STD\ (dP))^2$ integrated over a 5 second interval. Whereby, 'STD' is a statistical standard-deviation function measurement, 'dP' is the phase delta over the interval 'i', and W(i) is the resulting weight coefficient. The weighting represents an inverse relationship between noise, which is modelled as exhibiting randomized, uncoherent qualities and having a high standard deviation, and the differentially filtered heart rate signal, which is slowly changing but coherent. The weighting module 120 then applies a moving window to this weighting to update each of the ROI signals weighting for the specific interval. The contribution of the signal, representing the BPM estimate, from individual ROI signal banks will each be scaled by the respective weighting output. The scaling will be inversely proportional to the magnitude of each signal's calculated weights. In further cases, a different interval may be used, for example, 1 second, 2, second, 10 second, or the like.

All ROI signal banks will terminate their respective output signals, representing the instantaneous BPM estimate, at the summation module 122. At block 216, the summation module 122 will determine the average BPM based on the adaptively scaled contributions from all the ROIs. At block 218, the output module 124 will then output the calculated average BPM to an output device; for example, to a computer monitor, an LCD screen on a wearable device, or the like.

Applicant recognized the substantial advantages of using a multi-dimensional approach, as described herein, which offers the benefits of both 'spatial' diversity and 'time' diversity. Spatial diversity allows ROI signals to be acquired from non-overlapping differentially located regions on the human subject's face. 'Time' diversity allows accumulation of time-series data which is simultaneously sampled with a synchronous or fixed timing. Applicant recognized that a significant advantage of this approach being that the quality of the BPM estimate is more robust to noise interference (for example outlier data), and therefore more accurate than conventional approaches, while retaining the ability to update the output BPM value at every sample interval (in this example, at the video frame rate).

As an example, outlier data can distort the HC determinations and due to, for example, uneven lighting conditions on the face, slowly changing shadows moving across the face, or fixed facial obfuscations such as wrinkles, glasses, hair, and the like. With the multi-dimensional approach, as described herein, leveraging the spatial dimension by measuring the same signal at different points on the subject's face, the system is able to reject inconsistent or outlier data. As an example, having the ROI signal chains capturing approximately the same global heart-beat signal from 17 different points on the subject's face. In some cases, an average of the 17 ROI signals, with equal weighting, may reduce some outlier effects. As a further refinement, and for further accuracy, the multi-dimensional approach, as described herein, applies a weighted average to determine heart rate, whereby the weights being adaptively calculated to minimize data which has higher volatility.

In further embodiments, the system 100 could use an asynchronous sample rate. The asynchronous sample rate can capture HC data from images at a rate not synchronized or coupled with the video frame-rate. For example, capture the HC data at approximately 1 hertz, meaning 1 beat-per-second or 60 BPM nominal rate. Then, according to the Nyquist sampling theory, sampling at a minimum of twice the highest signal rate. For example, sampling at 5 hertz (or 5 frames per second), which would be much higher than required. In addition, this sampling would have the benefit of allowing the system 100 to only have to process 5 frames-per-second, rather than the more computationally intensive rates such as 30 fps or 60 fps.

In further embodiments, the camera can be directed to the skin of different body parts, such as for example the wrist or neck. From these body areas, the system may also extract dynamic hemoglobin changes to determine blood flow, and thus acquire heart rate as described herein. In some cases, optical sensors pointing, or directly attached to the skin of any body parts such as for example the wrist or forehead, in the form of a wrist watch, wrist band, hand band, clothing, footwear, glasses or steering wheel may be used. From these body areas, the system may also extract blood flow data for heart rate determinations.

In still further embodiments, the system may be installed in robots and their variables (e.g., androids, humanoids) that interact with humans to enable the robots to track heart rate on the face or other-body parts of humans whom the robots are interacting with.

The foregoing system and method may be applied to a plurality of fields. In one embodiment the system may be installed in a smartphone device to allow a user of the smartphone to measure their heart rate. In another embodiment, the system may be provided in a video camera located in a hospital room to allow the hospital staff to monitor the heart rate of a patient without requiring invasive monitors.

Further embodiments can be used in police stations and border stations to monitor the heart rate of suspects during interrogation. In yet further embodiments, the system can be used in marketing to see the heart rate changes of consumers when confronted with specific consumer goods.

Other applications may become apparent.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A method for camera-based heart rate tracking of a human subject, the method comprising:
   receiving a captured image sequence of light re-emitted from the skin of the human subject;
   determining, using a machine learning model trained with a hemoglobin concentration (HC) changes training set, HC changes of the subject;
   determining a blood flow data signal for each of a plurality of predetermined regions of interest (ROIs) of the subject captured by the images based on the HC changes;
   determining an instantaneous heart rate for each the blood flow data signals;
   applying a weighting to each of the instantaneous heart rates;
   averaging the weighted instantaneous heart rates; and
   outputting the average heart rate.

2. The method of claim 1, wherein the ROIs are captured from one or more of: the face, the wrist or the neck of the subject.

3. The method of claim 1, wherein the ROIs are non-overlapping.

4. The method of claim 1, wherein the HC changes of the subject are represented by bit values from a set of bitplanes in the captured image sequence, the set of bitplanes being those that are determined to approximately maximize a signal-to-noise ratio (SNR), the HC changes training set comprising bit values from each bitplane of images captured from a set of subjects for which heart rate is known.

5. The method of claim 4, wherein determining the set of bitplanes that maximize SNR comprises:
   performing pixelwise image subtraction and addition of bitplane vectors to maximize signal differences in all ROIs over a predetermined time period;
   identifying bit values from bitplanes that increase the signal differentiation and bit values from bitplanes that decrease the signal differentiation or do not contribute to signal differentiation; and discarding the bit values from the bitplanes that decrease the signal differentiation or do not contribute to signal differentiation.

6. The method of claim 1, wherein the machine learning model comprises a Long Short Term Memory (LSTM) neural network or a non-linear Support Vector Machine.

7. The method of claim 1, wherein the method further comprises applying a band-pass filter of a passband approximating the heart rate to each of the blood flow data signals, the passband being in a range of approximately 0.6 hertz to 1.2 hertz, where 60 heartbeats-per-minute is equivalent to 1 hertz.

8. The method of claim 1, wherein determining the instantaneous heart rate for each the blood flow data signals comprises adjusting the blood flow data signals from revolving phase-angles into linear phase segments, and applying a differential filter to the linear phase segments to convert phase-angle data into frequency units representing a count value, the count value for each of the ROIs represents the instantaneous heart rate.

9. The method of claim 8, further comprising linearizing and differentiating the revolving phase-angles on a phase continuum scale to determine the instantaneous heart rate.

10. The method of claim 1, wherein the weighting is integrated over an interval in the range of approximately one second to ten seconds.

11. A system for camera-based heart rate tracking of a human subject, the system comprising one or more processors and a data storage device, the one or more processors configured to execute:
    a TOI module configured to:
        receive a captured image sequence of light re-emitted from the skin of a human subject;
        determine, using a machine learning model trained with a hemoglobin concentration (HC) changes training set, HC changes of the subject; and
        determine a blood flow data signal for each of a plurality of predetermined regions of interest (ROIs) of the subject captured by the images based on the HC changes;
    a derivative module to determine an instantaneous heart rate for each the blood flow data signals;
    a weighting module to apply a weighting to each of the instantaneous heart rates;
    a summation module to average the weighted instantaneous heart rates; and
    an output module to output the average heart rate.

12. The system of claim 11, wherein the ROIs are captured from one or more of: the face, the wrist or the neck of the subject.

13. The system of claim 11, wherein the ROIs are non-overlapping.

14. The system of claim 11, wherein the HC changes of the subject are represented by bit values from a set of bitplanes in the captured image sequence, the set of bitplanes being those that are determined to approximately maximize a signal-to-noise ratio (SNR), the HC changes training set comprising bit values from each bitplane of images captured from a set of subjects for which heart rate is known.

15. The system of claim 14, wherein the TOI module determines a set of bitplanes that maximize SNR by:
    performing pixelwise image subtraction and addition of bitplane vectors to maximize signal differences in all ROIs over a predetermined time period;
    identifying bit values from bitplanes that increase the signal differentiation and bit values from bitplanes that decrease the signal differentiation or do not contribute to signal differentiation; and
    discarding the bit values from the bitplanes that decrease the signal differentiation or do not contribute to signal differentiation.

16. The system of claim 11 further comprising a band-pass filter having a passband approximating the heart rate applied to each of the blood flow data signals, wherein the passband is in a range of approximately 0.6 hertz to 1.2 hertz, where 60 heartbeats-per-minute is equivalent to 1 hertz.

17. The system of claim 11, wherein the derivative module determines the instantaneous heart rate for each the blood flow data signals by adjusting the blood flow data signals from revolving phase-angles into linear phase segments, and applying a differential filter to the linear phase segments to convert the phase-angle data into frequency units representing a count value, the count value for each of the ROIs represents the instantaneous heart rate.

18. The system of claim 17, wherein the derivative module linearizes and differentiates the revolving phase-angles on a phase continuum scale to determine the instantaneous heart rate.

19. The system of claim 11, wherein the weighting applied by the weighting module is integrated over an interval in the range of approximately one second to ten seconds.

20. The system of claim 11, wherein the weighting applied by the weighting module is integrated over an interval of approximately five seconds.

* * * * *